USO09846169B2

(12) United States Patent
Burri et al.

(10) Patent No.: US 9,846,169 B2
(45) Date of Patent: Dec. 19, 2017

(54) SYSTEM AND METHOD FOR STORING AND RETRIEVING VESSEL HOLDERS

(71) Applicant: Roche Diagnostics Operations, Inc., Indianapolis, IN (US)

(72) Inventors: Martin Burri, Bettwil (CH); Andreas Eberhart, Oberwil b. Zug (CH); Akihiro Tanji, Kanagawa Pref. (JP)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 297 days.

(21) Appl. No.: 14/055,218

(22) Filed: Oct. 16, 2013

(65) Prior Publication Data

US 2014/0109527 A1    Apr. 24, 2014

(30) Foreign Application Priority Data

Oct. 24, 2012 (EP) .................................... 12189683

(51) Int. Cl.
  *G01N 35/00* (2006.01)
  *G01N 35/04* (2006.01)
(52) U.S. Cl.
  CPC ............. *G01N 35/00* (2013.01); *G01N 35/04* (2013.01); *G01N 2035/0412* (2013.01); *G01N 2035/0462* (2013.01); *G01N 2035/0465* (2013.01)
(58) Field of Classification Search
  CPC ..................................................... G01N 35/04
  See application file for complete search history.

(56) References Cited

U.S. PATENT DOCUMENTS 4,113,436 A * 9/1978 Werder ................ G01N 35/021
                                                          422/65
4,120,662 A * 10/1978 Fosslien ................ G01N 35/04
                                                          422/561
(Continued)

FOREIGN PATENT DOCUMENTS

JP      S60-154834 U1    10/1985
JP      H04-319667 A     11/1992
(Continued)

*Primary Examiner* — Sean E Conley
*Assistant Examiner* — Matthew Krcha
(74) *Attorney, Agent, or Firm* — Roche Diagnostics Operations, Inc.

(57) ABSTRACT

An automated system and method for storing/retrieving vessel holders is presented. A first storage compartment comprises first storage sections. A first translating mechanism vertically translates one storage section to a loading level for loading holders into the first storage compartment and translates one storage section to a handing-in level for handing in holders to/from an analyzer. A second storage compartment comprises second storage sections. A second translating mechanism vertically translates one second storage sections to a handing-out level and translates one storage section to an unloading level for unloading holders from the second storage compartment. A first transport mechanism comprises a first conveyor for transporting holders from a first storage section at the handing-in level to a handing-over station. A second transport mechanism comprises a second conveyor for transporting holders from the handing-over station to a second storage section at the handing-out level. A controller operates the mechanisms.

14 Claims, 3 Drawing Sheets

(56) References Cited

U.S. PATENT DOCUMENTS

| | | |
|---|---|---|
| 5,232,081 A | 8/1993 | Kanamori |
| 5,623,415 A * | 4/1997 | O'Bryan ............... G01N 35/021 198/617 |
| 5,682,026 A * | 10/1997 | Auclair .................. G01N 35/04 235/375 |
| 2001/0029320 A1* | 10/2001 | Trumbull ............. G01N 35/028 600/300 |
| 2002/0012611 A1* | 1/2002 | Stylli ........................ B01J 19/00 422/65 |
| 2004/0212285 A1* | 10/2004 | Melching .................. B01L 9/52 312/352 |
| 2005/0196320 A1 | 9/2005 | Veiner et al. |
| 2006/0210435 A1* | 9/2006 | Alavie ................. G01N 21/253 422/65 |
| 2007/0172396 A1 | 7/2007 | Neeper et al. |
| 2009/0003981 A1 | 1/2009 | Miller |
| 2011/0158850 A1 | 6/2011 | Pedrazzini |

FOREIGN PATENT DOCUMENTS

| | | |
|---|---|---|
| JP | H05-9355 Y2 | 3/1993 |
| JP | H06-074958 A | 3/1994 |
| JP | 2005-274153 A | 10/2005 |
| JP | 2007-309675 A | 11/2007 |
| JP | 2012-021911 A | 2/2012 |
| WO | 98-52046 A1 | 11/1998 |
| WO | 02/086514 A3 | 10/2002 |
| WO | 2009/002358 A1 | 12/2008 |
| WO | 2009/077465 A1 | 6/2009 |

* cited by examiner

SYSTEM AND METHOD FOR STORING AND RETRIEVING VESSEL HOLDERS

CROSS-REFERENCE TO RELATED APPLICATIONS

This application is a continuation of EP 12189683.1, filed Oct. 24, 2012, which is hereby incorporated by reference.

BACKGROUND

The present disclosure generally relates to the field of analytical sample processing and, in particular, to the field of analytical sample processing comprising a system and method for storing and retrieving of vessel holders.

In automated clinical analyzers liquid samples, such as bodily fluids, can be tested by various clinical-chemical and immunochemical methods. Modern analyzers typically can be loaded with many samples in a batch-wise manner in order to process the samples of one batch automatically. With commercially available analyzers, the samples typically can be loaded into a dedicated loading space so that the number of samples which can be fed to the analyzer by one batch usually cannot be increased without enlarging the overall dimensions of the analyzer.

In daily routine, however, a situation may arise where more samples than can be fed into the analyzer by one batch are supposed to be processed. Hence, the technician has to distribute the samples over multiple batches and consequently has to wait until a running batch is ready to be removed from the analyzer before the next batch can be fed into the analyzer. However, this course of action needs much attention by the technician and is rather time consuming as each batch must be handled individually. Furthermore, it can lead to unoccupied times of the analyzer since the technician is not always available to attend to the analyzer right after the stop of an on-going run. Furthermore, with conventional analyzers, samples normally cannot be localized and removed from the analyzer until the on-going run is completed.

Therefore, there is a need to improve feeding and removing of samples to/from the analyzer in order to increase or decrease the capacity of samples that can be fed into the analyzer according to the specific demands of the user without affecting the overall dimensions of the analyzer as well as to localize the individual samples before being loaded into the analyzer.

SUMMARY

According to the present disclosure, an automated system and method for storing and retrieving of vessel holders for holding sample vessels containing samples is presented. A first storage compartment can comprise a plurality of first storage sections disposed on different levels for storing of vessel holders. A first translating mechanism can vertically translate the first storage sections so as to translate one storage section at a time to a loading level of a loading zone for loading vessel holders into the first storage compartment and to translate one storage section at a time to a handing-in level of a handing-over station for handing in vessel holders to at least one analyzer for analyzing the samples. A second storage compartment can comprise a plurality of second storage sections disposed on different levels for storing of vessel holders. A second translating mechanism can vertically translate the second storage sections so as to translate one storage section at a time to a handing-out level of the handing over station and to translate one storage section at a time to an unloading level of an unloading zone for unloading vessel holders from the second storage compartment. A first transport mechanism can comprise a first conveyor for transporting vessel holders from a first storage section at the handing-in level to the handing-over station. A second transport mechanism can comprise a second conveyor for transporting vessel holders from the handing-over station to a second storage section at the handing-out level. A controller can operate the mechanisms.

Accordingly, it is a feature of the embodiments of the present disclosure to improve feeding and removing of samples to/from the analyzer in order to increase or decrease the capacity of samples that can be fed into the analyzer according to the specific demands of the user without affecting the overall dimensions of the analyser as well as to localize the individual samples before being loaded into the analyzer. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A new automated system for storing and retrieving of vessel holders is presented. The system can be configured in various ways in accordance with specific demands of the user and, for example, can be particularly useful in connection with automated analyzers for analyzing samples by various analytical methods such as, but not limited to, clinical-chemical, immunochemical, and biochemical analysis items.

The term "sample," as used herein, can refer to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like. Methods of treatment can involve filtration, distillation, concentration, inactivation of interfering components, and the addition of reagents. A sample may be used directly as obtained from the source or following a pre-treatment to modify the character of the sample, for example, after being diluted with another solution or after having been mixed with reagents, for example, to carry out one or more diagnostic assays like clinical chemistry assays, immunoassays, coagulation assays, nucleic acid testing, and the like. The term "sample" as used herein can therefore not be only used for the original sample but also can relate to a sample which has already been processed (pipetted, diluted, mixed with reagents, enriched, having been purified, having been amplified and the like). Samples may be liquid solutions in which one or more analytes of interest can be potentially found. Biological samples can relate to materials that can be subjected to a diagnostic assay targeting nucleic acids and can be usually derived from a biological source. In some embodiments, biological samples can be derived from a human and can be body liquids, such as, but not limited to, human blood, urine, sputum, sweat, swab, pipettable stool, or spinal fluid.

According to one embodiment, the system can include a first storage compartment and a second storage compartment, with the first storage compartment comprising a plurality of first storage sections disposed on different levels and the second storage compartment comprising a plurality of second storage sections disposed on different levels. The storage sections can store vessel holders for holding sample vessels containing samples. In particular, a "storage section" can be a horizontal platform or frame mounted in a storage compartment and geometrically configured to receive one or more vessel holders arranged next to each other. In one embodiment, each of the first and second storage sections can be a modular unit.

As used herein, the term "vessel holder" can relate to any device capable of holding one or more sample vessels in vessel positions. Each sample vessel can be held in one vessel position. As used herein, the term "vessel position" can relate to a region of the vessel holder adapted for holding one sample vessel. In one embodiment, the vessel position can be adapted to the geometry (outer shape) of the sample vessel and, for example, can be a rack seat, and in one alternative embodiment may not be adapted to the geometry of the sample vessel and, for example, can be a flat surface.

In one embodiment, the vessel holder can comprise one or more racks, each of which can hold one or more sample vessels, for example, in a linear arrangement. In one embodiment, one or more racks can be located on a tray adapted to arrange one or more racks and/or one or more single vessel holders. The tray can be provided with one or more rack positions for holding racks. As used herein, the term "rack position" can relate to a region of the tray for holding one rack which, in one embodiment, can be adapted to the geometry (outer shape) of the rack, and, in one alternative embodiment, may not be adapted to the geometry of the rack. In one embodiment, the tray can be a drawer removably insertable into the first and/or second storage section.

In one embodiment, the holder can comprise one or more single vessel holders (for example, single tube holders), each of which can hold one sample vessel (for example, single tube).

In one embodiment, the vessel holder can comprise a combination of one or more racks and one more single vessel holders. In one embodiment, one or more racks and one or more single vessel holders can be located on a tray comprising one or more rack positions for holding racks and one or more single vessel holder positions for holding single vessel holders.

As used herein, the term "sample vessel" can relate to any device capable of containing one sample. In one embodiment, the sample vessel can be a sample tube.

The system can further include a first translating mechanism operatively coupled to the first storage sections for vertically translating the first storage sections. Specifically, when operating the first translating mechanism, one first storage section at a time can be translated to a loading level of a loading zone for loading vessel holders into the first storage compartment. The first translating mechanism can also be used to translate one first storage section at a time to a handing-in level of a handing-over station for handing in vessel holders to at least one analyzer for analyzing the samples.

The system can further include a second translating mechanism operatively coupled to the second storage sections for vertically translating the second storage sections. Specifically, when operating the second translating mechanism, one second storage section at a time can be translated to a handing-out level of the handing over station. The second translating mechanism can also be used to translate one second storage section at a time to an unloading level of an unloading zone for unloading vessel holders from the second storage compartment.

In one embodiment, the first and second translating mechanisms can be one translating mechanism. In one embodiment, the first and second translating mechanisms can be two translating mechanisms different with respect to each other. In one embodiment, the first and second translating mechanisms can be operated independently from each other.

The system can further include a first transport mechanism operatively coupled to the first storage sections and a second transport mechanism operatively coupled to the second storage sections. The first transport mechanism can comprise a first conveyor for transporting vessel holders from one first storage section at the handing-in level to the handing-over station. The second transport mechanism can comprise a second conveyor for transporting vessel holders from the handing-over station to one second storage section at the handing-out level. In one embodiment, the first and second transport mechanisms can be operated independently from each other.

The system can also include a controller for controlling the various components of the system. Such controller may be a separate unit or may be an integral part of a system component. The controller can control the system in a way that the storing and retrieving of vessel holders can be conducted. That can mean, the controller, for example, can instruct the first translating mechanism, the first transport mechanism, the second translating mechanism, the second transport mechanism and the second translating mechanism. In one embodiment, the controller can be a programmable logic controller running a computer-readable program provided with instructions to perform operations in accordance with a process operation plan.

In one embodiment, the controller can include a data base for reading/writing inventory information with respect to samples and/or sample vessels and/or vessel holders.

The data base can be used for reading/writing position information of one or more sample vessels with respect to the vessel holder holding the sample vessels and/or position information of one or more vessel holders. As used herein, the term "position information" can relate to information of the position of one or more samples vessels on one vessel holder. Since each vessel holder can hold one or more sample vessels in dedicated vessel positions, each sample vessel can be associated with one vessel position so as to obtain a one-to-one relationship between sample vessels and vessel positions on the vessel holder. Since there can be a regularly known one-to-one relationship between samples and sample vessels, the position information can also relate to information of the position of one or more samples on one vessel holder. The term "position information" can further relate to the position of individual vessel holders in the system.

As used herein, the term "inventory information" can relate to the position information of sample vessels and/or vessel holders. It can also relate to further information related to one or more sample vessels. Specifically, the information related to one sample vessel may comprise a variety of data, for example, sample identity (ID), vessel ID, patient ID, sample date, kind of sample, which analysis is to be performed or has yet to be performed and the like. As used herein, the term "inventory" can relate to the inventory information stored as a whole in the data base or in a memory tag as described further below. Accordingly, sample vessels and vessel holders can readily be located and traced by the inventory.

In one embodiment, the controller can operate the first translating mechanism for translating a first storage section one at a time to the loading level for loading of vessel holders in the first storage compartment and for translating holder-loaded first storage sections one at a time to the handing-in level; the first transport mechanism for transporting vessel holders from the holder-loaded first storage sections, translated one at a time to the handing-in level, to the handing-over station; the second translating mechanism for translating second storage sections one at a time to the handing-out level; the second transport mechanism for transporting vessel holders from the handing-over station to the second storage sections, translated one at a time to the handing-out level; and the second translating mechanism for translating holder-loaded second storage sections one at a time to the unloading level for unloading of vessel holders from the second storage compartment.

Accordingly, sample vessels can be stored in two storage compartments. One can be used for loading sample vessels into the system and handing them in to the handing-over station and the other one can be used for handing sample vessels out from the handing-over station and unloading the sample vessels from the system. Due to the three-dimensional loading of the sample vessels in many levels combined with a vertical translating mechanism to selectively position individual storage sections in specific levels, a bigger or smaller number of samples can be stored in the storage compartments according to the specific demands of the user. Specifically, the storing capacity of the storage compartments can readily be increased/decreased by adding/ removing storage sections stacked one upon the other in various storage levels. Furthermore, samples can readily be loaded/unloaded to/from the system without affecting operation of the analyzer so that samples can even be handled during an on-going run.

In one embodiment, the controller can be configured in such a manner that a vessel holder can be handed in from a first storage section to the handing-over station only when there is at least one empty position available in a second storage section for receiving the vessel holder from the handing-over station.

In one embodiment, in which the vessel holder can include a tray, the first and/or second storage section can have the tray for holding a plurality of vessel holders. The tray can be insertable into and removable from the storage compartment through the loading zone and/or unloading zone. Accordingly, loading and unloading with samples can be handled via the tray.

In one embodiment, the first and/or second storage sections can be insertable into and removable from the storage compartments through the loading zone and/or unloading zone. Accordingly, the number of storage sections can readily be increased or decreased according to the specific demands of the user. Furthermore, storage sections can be loaded and/or unloaded outside the storage compartments.

In one embodiment, each of the storage sections can be positioned in various levels so that inter-distance between two adjacent storage sections can be changed. Accordingly, the inter-distance between two adjacent storage sections can readily be adapted to the specific demands of the user, for example, to adapt it to the height of sample vessels or to reduce the inter-distance to accommodate more storage sections in the storage compartments.

In one embodiment, the first and second conveyors can be unidirectional conveyors. Accordingly, the vessel holders can readily be transported between the storage compartments and the handing-over station, with the transport of vessel holders from the first storage section at the handing-in level to the handing-over station not affected by the transport of vessel holders from the handing-over station to the second storage compartment at the handing-out level.

In one embodiment, the first conveyor can have a decapping unit for decapping sample vessels and/or the second conveyor can have a recapping unit for recapping sample vessels. Accordingly, sample vessels can readily be prepared for testing by the analyzer and/or unloading from the system.

In one embodiment, the storage compartments can be coupled to a cooling device for actively cooling samples contained therein. Accordingly, samples can be cooled during storage prior to and after testing by the analyzer so as to avoid degradation of the samples and to increase the reliability of test results. The cooling can allow samples to be stored over a longer period of time prior to and after testing by the analyzer.

In the system of the invention, an information tag can be attached to one or more vessel holders and/or one or more sample vessels for storing and/or retrieving machine-readable information, for example, position information of sample vessels with respect to the vessel holder holding the sample vessels. In one embodiment, the information tag can be a memory tag. As used herein the term "memory tag" can indicate an information storage device which can be used to store (write) information thereon and to read the stored information. In one embodiment, the memory tag can be selected from an RFID-tag, a magnetic storage tag, a memory chip and the like. Specifically, the memory tag can be used to indicate a sample ID (ID=identity) of sample contained in a sample vessel and/or a sample vessel ID and/or vessel holder ID. Furthermore, information with respect to samples such as, but not limited to, sample date, patient name and the like can be stored in the memory tag.

In one embodiment, one or more sample vessels and/or one or more vessel holders respectively can have a read-only tag (without writing function) containing machine-readable information for reading information such as sample ID and further information related to the sample such as sample date and patient name.

In one embodiment, in which the holder can comprise one or more racks and/or one or more single vessel holders (for example, single tube holders) located on a tray, the memory tag can be attached to the tray and/or each rack and/or each single vessel holder and/or each sample vessel. Specifically, the memory tag can be attached to the tray and each sample vessel. Specifically, the memory tag can be attached to the tray. Each sample vessel can have a read-only tag such as, but not limited to, a barcode label. Specifically, the memory tag can be attached to the tray. Each sample vessel and/or each rack and/or each single vessel holder can have a read-only tag such, but not limited to, a barcode label.

Accordingly, an (newly generated) arrangement of sample vessels with respect to the vessel positions of one vessel holder can be stored in the memory tag of the vessel holder to be retrieved later for locating individual sample vessels. It, thus, may not be necessary to keep a specific arrangement of sample vessels with respect to the vessel positions of one vessel holder which strongly facilitates sample processing, for example, in a case in which samples are processed in a different manner. In one embodiment, in which one or more sample vessels can be put on one rack, each of the one or more sample vessels can remain in a same position with respect to the rack.

In one embodiment, a memory tag can be changed to a read-only tag, for example, by fusing a conductor contained in the memory tag. In one embodiment, information contained in a memory tag can be secured, for example, by encrypting or by checksums in order to prevent changing and/or reading the information contained therein.

In one embodiment, the system can comprise at least one reader/writer for reading/writing information such as inventory information from/into memory tags and/or reading information from read-only tags. In one embodiment, the reader/writer can be used for reading/writing inventory information into memory tags for making an inventory. Specifically, sample vessels can be located and traced by reading/writing information from/into memory tags and/or reading information from read-only tags.

In one embodiment, the system can comprise at least one reader/writer in the first storage compartment, for example, in the loading zone for reading information from memory tags and/or read-only tags and/or writing information such as inventory information into memory tags and/or into the database of the controller. In one embodiment, the controller can operate the reader/writer in the first storage compartment to read information from memory tags and/or read-only tags on sample vessels on a tray and to write inventory information with respect to the tray into a memory tag attached to the tray and/or into the database of the controller.

Specifically, in one embodiment, the system can comprise at least one reader/writer in the second storage compartment, for example, in the unloading zone, for reading information from memory tags and/or read-only tags and/or writing information such as inventory information into memory tags. In one embodiment, the controller can operate the reader/writer in the second storage compartment to read information from memory tags and/or read-only tags on sample vessels on a tray and to write inventory information with respect to the tray into a memory tag attached to the tray. Accordingly, inventory information can be written on the memory tag of the tray before unloading the tray from the second storage compartment.

In one embodiment, the controller can operate the one or more reader/writers for reading information from memory tags and/or read-only tags attached to sample vessels and/or vessel holders for locating and/or tracing sample vessels and/or vessel holders in the first and/or second storage sections.

In one embodiment, the controller can operate the one or more reader/writers for writing information into memory tags attached to sample vessels and/or vessel holders for making an inventory and tracing the sample vessels and/or vessel holders.

In one embodiment, the controller can identify inventory information of vessel holders stored in the controller database to allow locating and/or tracing of individual vessel holders and/or individual sample vessels in the first or second storage sections.

In one embodiment, the controller can communicate with the analyzer so as to exchange inventory information with respect to vessel holders. Specifically, the controller can receive inventory information from the analyzer with respect to vessel holders and update the inventory of the database with that inventory information. Accordingly, the controller can locate and trace the position of each sample vessel and/or vessel holder contained in the first or second storage compartment or in the analyzer based on the inventory information stored in the inventory of the database. Specifically, the inventory can be used to control loading of vessel holders into the first storage compartment and/or to control unloading of vessel holders from the second storage compartment. In one embodiment, the controller can control loading/unloading of vessel holders based on the inventory information of vessel holders, for example, contained in the analyzer, so as to specify an order for loading/unloading vessel holders in a highly efficient manner.

In one embodiment, the system can comprise one or more sensors for sensing if the storage sections are in a loaded, in a partially unloaded or in an unloaded state. Accordingly, storage sections can be selectively vertically translated to specific levels, in particular for loading/unloading vessel holders and/or handing in/handing out vessel holders.

In one embodiment, the system can comprise a sorting device for sorting sample vessels into a vessel holder, with the sorting device coupled to a writer set up to write information related to the positions of the sorted sample vessels into the memory tag of the vessel holder.

In one embodiment, the controller can control a loading mode initiated by user interaction in which the first transport mechanism can be paused and the first translating mechanism can be operated for translating one or more first storage sections one at a time to the loading level for loading the first storage compartment with vessel holders. In one embodiment, the controller can control an unloading mode initiated by user interaction in which the second transport mechanism can be paused and the second translating mechanism can be operated for translating one or more holder-loaded second storage sections one at a time to the unloading level for unloading of vessel holders from the second storage compartment.

According to one embodiment, a modular analytical system is proposed. The system can comprise an automated system for storing and retrieving of vessel holders as described above, at least one analyzer for analyzing samples and a handing-over station for handing over vessel holders from the first storage compartment to the analyzer and from the analyzer to the second storage compartment.

In one embodiment of the modular analytical system, the handing-over station can comprise a buffer and/or a bypass section for temporarily storing vessel holders before handing them over to the analyzer and/or for handing over vessel holders to the second storage compartment bypassing the analyzer.

According to one embodiment, an automated method for storing and retrieving of vessel holders is proposed. The method can be configured in various ways in accordance with specific demands of the user and, for example, can be used in connection with at least one automated analyzer related to various analytical methods. Specifically, the method of the invention can be used in a system as described above.

The method can comprise vertically translating first storage sections disposed on different levels for translating one storage section at a time to a loading level for loading of vessel holders. One holder-loaded first storage section at a time can be vertically translated to a handing-in level of a handing-over station for handing in vessel holders to/from an analyzer for analyzing the samples. Vessel holders can be transported from the holder-loaded first storage sections at the handing-in level to the handing-over station. Second storage sections can be vertically translated disposed on different levels for translating one storage section at a time to a handing-out level of the handing-over station. Vessel holders can be transported from the handing-over station to the second storage sections at the handing-out level. One holder-loaded second storage section at a time can be vertically translated to an unloading level of an unloading zone for unloading vessel holders.

In one embodiment, the second storage sections can be vertically translated independently from the first storage sections.

In one embodiment, the method can comprise a loading mode that can pause transporting of vessel holders from the holder-loaded first storage sections to the handing-over station and can vertically translate one or more first storage sections one at a time to the loading level for loading with vessel holders.

In one embodiment, the loading mode can be performed in parallel to vertically translating one or more second storage sections one at a time to the handing-out level, to transporting vessel holders from the handing-over station to the second storage sections at the handing-out level, and to vertically translating one or more holder-loaded second storage sections one at a time to the unloading level for unloading of vessel holders.

In one embodiment, the method can comprise an unloading mode that can pause transporting of vessel holders from the handing-over station to the second storage sections and can vertically translate one or more holder-loaded second storage sections one at a time to the unloading level for unloading of vessel holders from the second storage compartment.

In one embodiment, the unloading mode can be performed in parallel to vertically translate one or more first storage sections one at a time to the loading level for loading of vessel holders, vertically translate holder-loaded first storage sections one at a time to the handing-in level and transport vessel holders from the holder-loaded first storage sections at the handing-in level to the handing-over station.

In one embodiment, the method can comprise reading information from memory tags and/or read-only tags attached to vessel holders and/or sample vessels so as to identify the vessel holders and/or sample vessels. Individual vessel holders and/or sample vessels can be located and/or traced based on information read from memory tags and/or read-only tags. Individual vessel holders and/or sample vessels can be located and/or traced based on information located in a controller database. Inventory information can be written into memory tags attached to sample vessels and/or vessel holders for making an inventory and tracing sample vessels and/or vessel holders. Inventory information can be written into a controller database for making an inventory and tracing sample vessels and/or vessel holders. An unloaded or partially unloaded first storage section to be next translated to the loading level can be determined, for example, based on a shortest distance of unloaded first storage sections to the loading level. A holder-loaded first storage section to be next translated to the handing-in level can be determined, for example, based on a shortest distance to the handing-in level or on a longest storing time of the vessel holders loaded on the first storage sections. An unloaded or partially unloaded second storage section to be next translated to the handing-out level can be determined, for example, based on a shortest distance to the handing-out level. A holder-loaded second storage section to be next translated to the unloading level can be determined, for example, based on a shortest distance of holder-loaded second storage sections to the unloading level or on a longest storing time of the vessel holders loaded on the second storage sections. If the first and second storage sections are in a loaded or unloaded or partially unloaded state can be sensed. Sample vessels can be decapped prior to transporting from the first storage sections at the handing-in level to the handing-over station. Sample vessels can be recapped prior to transporting from the handing-over station to the second storage sections at the handing-out level. Samples can be actively cooled stored in the first and second storage sections.

Specifically, in one embodiment, the method can include reading information from memory tags and/or read-only tags attached to vessel holders and/or sample vessels so as to identify vessel holders and/or sample vessels and a step of locating and/or tracing vessel holders and/or sample vessels based on information read from the tags and/or a step of writing inventory information into memory tags attached to sample vessels and/or vessel holders for making an inventory and tracing sample vessels and/or vessel holders.

Specifically, in one embodiment, the method can include locating and/or tracing individual vessel holders and/or sample vessels based on information located in a controller database and/or a step of reading information from memory tags and/or read-only tags attached to vessel holders and/or sample vessels so as to identify the vessel holders and/or sample vessels and a step of writing inventory information into the controller database for up-dating the inventory.

In one embodiment, the method can comprise reading information provided by memory tags and/or read-only tags of sample vessels on a vessel holder loaded on a first storage section and writing inventory information into a memory tag attached to the vessel holder and/or into a data base of a controller.

In one embodiment, the method can comprise reading information provided by memory tags and/or read-only tags of sample vessels on a vessel holder loaded on a second storage section and writing inventory information into a memory tag attached to the vessel holder and/or into a data base of a controller.

In one embodiment, information contained in the memory tag can be locked after writing into the memory tag so as to protect the content and to prevent access.

In one embodiment, a memory tag can be changed to a read-only tag after writing the information thereon so that the memory can only be used to read information stored therein without a possibility to change the stored information. Accordingly, information can readily be kept in the memory tag.

In one embodiment, information stored in the memory tag can be protected, for example, by encrypting or by checksums in order to prevent changing and/or reading of the information.

Figure 1A:
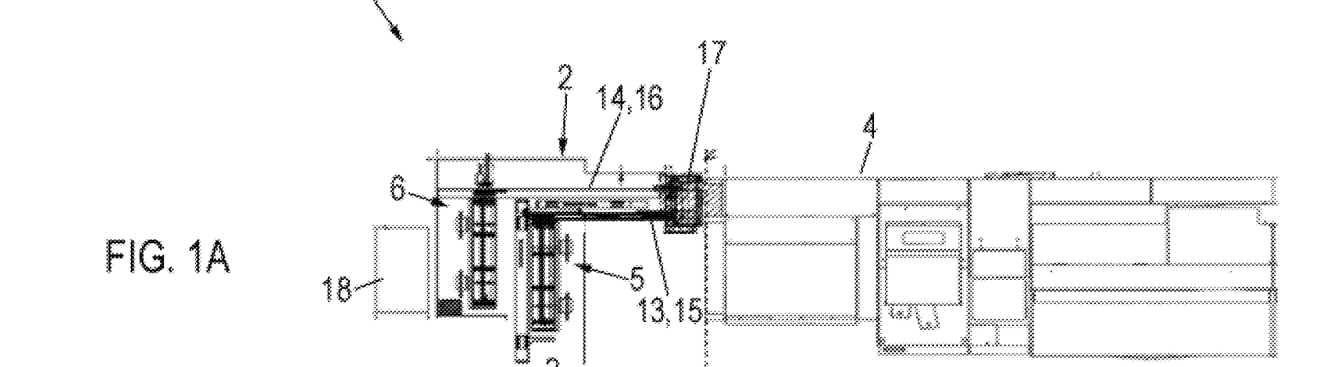
FIGS. 1A-B illustrate a schematic top view (FIG. 1A) and a schematic longitudinal side view (FIG. 1B) of an exemplary system for locating sample vessels according to an embodiment of the present disclosure.
Figure 1B:
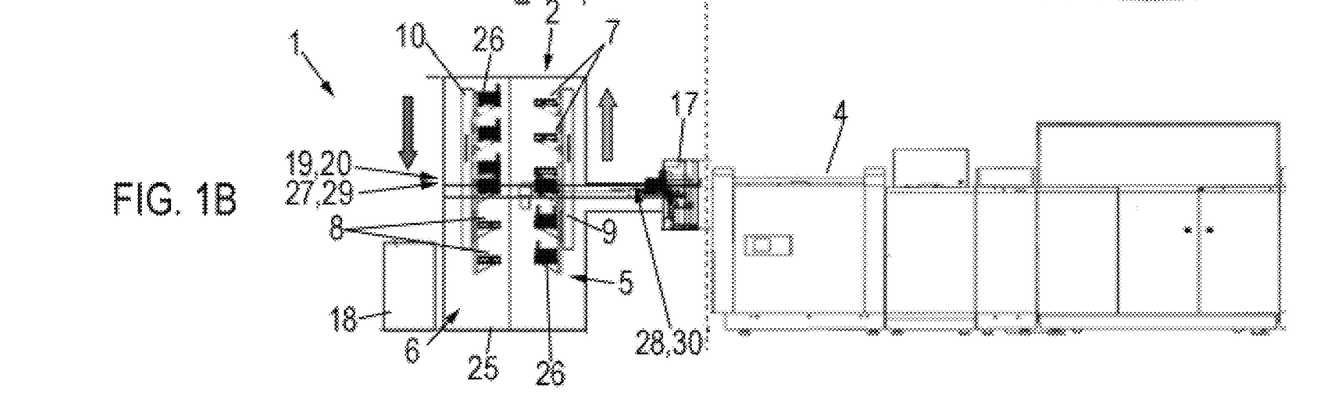

Referring initially to FIGS. 1A-B, FIGS. 1A-B illustrate a top view (FIG. 1A) and a side view (FIG. 1B) of an automated system for locating sample vessels generally referred to by reference numeral 1. Specifically, the system 1 can include an automated storing/retrieving device 2 for storing and retrieving of sample vessels 3 for containing samples. The storing/retrieving device 2 can be operatively coupled to an automated analyzer 4 for analyzing samples contained in the sample vessels 3.

The storing/retrieving device 2 can include a housing 25 enclosing two storage compartments 5, 6 for storing sample vessels 3. While two storage compartments 5, 6 are depicted for the purpose of illustration only, it is to be understood that a smaller or larger number of storage compartments can be envisaged according to the specific demands of the user. Specifically, a first storage compartment 5 can comprise a plurality of first storage sections 7 disposed on different, vertically spaced apart levels for storing of vessel holders 26 and a second storage compartment 6 can be arranged adjacent and side-to-side to the first storage compartment 5 can comprise a plurality of second storage sections 8 disposed on different, vertically spaced apart levels for storing of vessel holders 26. Each vessel holder 26 can hold a plurality of sample vessels 3. In one embodiment, each storage section 7, 8 can be fixed in various levels so as to change inter-distance between adjacent storage sections 7, 8 according to the specific demands of the user.

In the storing/retrieving device 2, each of the storage compartments 5, 6 can be operatively coupled to a translating mechanism 9, 10, respectively, with the first storage compartment 5 coupled to a first translating mechanism 9 for vertically translating the first storage sections 7 and the second storage compartment 6 coupled to a second translating mechanism 10 for vertically translating the second storage sections 8. The first and second translating mechanisms 9, 10 can be independently operated with respect to each other. Accordingly, by operating the first and second translating mechanisms 9, 10, the first and second storage sections 7, 8, respectively, can together be vertically translated so as to move individual storage sections 7, 8 to various levels.

Specifically, in the first storage compartment 5, one first storage section 7 at a time can be vertically translated to a loading level 27 of a loading zone 19 for loading vessel holders 26 into the first storage compartment 5. As illustrated, in one embodiment, the loading level 27 can be located in a middle portion of the housing 25 but can also be located in an upper portion and/or a lower portion of the housing 25. Furthermore, more than one loading zone 19, each of which having an individual loading level 27 can be envisaged according to the specific demands of the user. In the first storage compartment 5, one first storage section 7 at a time can be vertically translated to a handing-in level 28 for handing in vessel holders 26 from the first storage section 7 to a handing-over station 17 for handing over vessel holders 26 to the analyzer 4. In the second storage compartment 6, one second storage section 8 at a time can be vertically translated to a handing-out level 30 of the handing-over station 17 for handing out vessel holders 26 from the handing-over station 17 to the second storage section 8.

As illustrated, the handing-out level 30 can be identical to the handing-in level 28 but can also be different from the handing-in level 28. Furthermore, in the second storage compartment 6, one second storage section 8 at a time can be vertically translated to a unloading level 29 of a unloading zone 20 for unloading vessel holders 26 from the second storage compartment 6. As illustrated, the unloading level 29 can be identical to the loading level 27 but can also be different from the loading level 27. As further illustrated, in one embodiment, the unloading level 29 can be located in a middle portion of the housing 25 but can also be located in an upper portion and/or a lower portion of the housing 25. Furthermore, more than one unloading zone 20, each of which having an individual unloading level 29 can be envisaged according to the specific demands of the user.

Figure 3A:
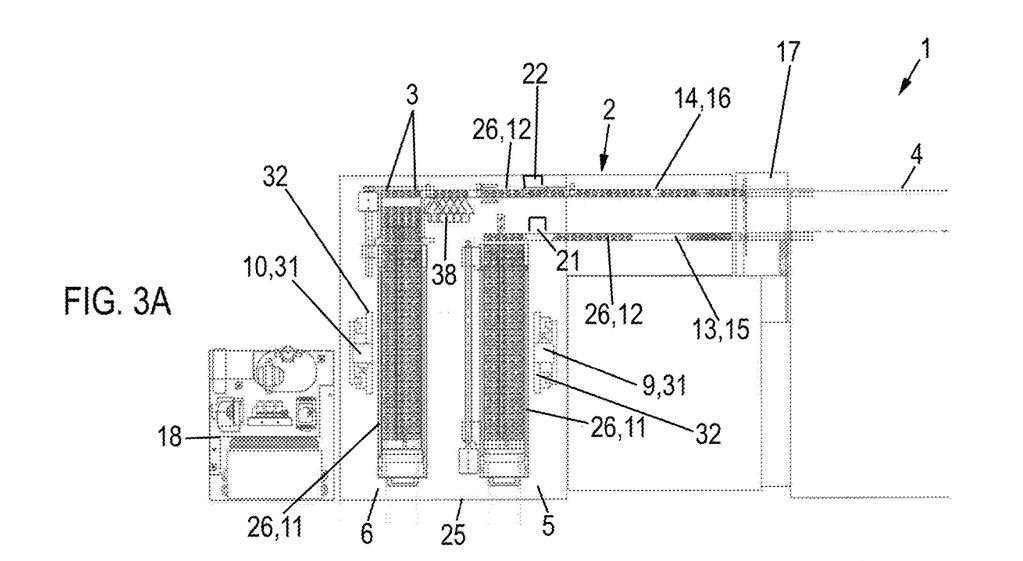
FIGS. 3A-C illustrate another schematic top view (FIG. 3A) of the system of FIGS. 1A-B illustrating more details, a schematic front view (FIG. 3B) and a schematic side view (FIG. 3C) of the storing/retrieving device of the system of FIGS. 1A-B according to an embodiment of the present disclosure.

The first and second translating mechanisms 9, 10 can be operated independently from each other so that the first storage sections 7 can be vertically translated without simultaneously vertically translating the second storage sections 8, and vice versa. As illustrated in FIG. 3A, in one embodiment, the first and second translating mechanisms 9, 10, respectively, can be constructed as geared elevators, each of which comprising a vertical rod 31 connected to a carrier 32 movably fixed to the rod 31, with the storage sections 7, 8 mounted to the carrier 32. In one embodiment, the carrier 32 can be in threaded engagement with the rod 31 so that the carrier 32 can be moved upwards or downwards by rotating the rod 31 along its longitudinal axis. As illustrated in FIG. 3C, an electric motor 33 can be used to rotate the rod 31. Likewise, any other mechanism can be used to vertically move the carrier 32 along the rod 31 such as, but not limited to, a hydraulic lift mechanism and a driven roller mechanism.

With continued reference to FIGS. 1A-B, in the system 1, the storing/retrieving device 2 can include a first transport mechanism 13 operatively coupled to the first storage compartment 5 comprising a first conveyor 15 for transporting vessel holders 26 from a first storage section 7 at the handing-in level 28 to the handing-over station 17. The first conveyor 15 can, for example, be a unidirectional conveyor for transporting vessel holders 26 from the first storage 7 to the handing-over station 17 but not in the reverse direction. In one embodiment, the first conveyor 15 can have a decapping unit 21 for decapping sample vessels 3 passing by.

The storing/retrieving device 2 can include a second transport mechanism 14 that can be independently operable from the first transport mechanism 13. The second transport mechanism 14 can be operatively coupled to the second storage compartment 6 and can comprise a second conveyor 16 in parallel to the first conveyor 15 for transporting vessel holders 26 from the handing-over station 17 to a second storage section 8 at the handing-out level 30. The second conveyor 16 can, for example, be a unidirectional conveyor for transporting vessel holders 26 from the handing-over station 17 to the second storage section 8 but not in the reverse direction. In one embodiment, the second conveyor 16 can have a recapping unit 22 for recapping sample vessels 3 passing by. The first and second conveyors 15, 16, respectively, can, for example, be constructed as driven conveyor belt which is well-known to the skilled person so that it is unnecessary to further elucidate it herein.

In order to transport vessel holders 26 from the first storage section 7 at the handing-in level 28 to the first conveyor 15 and from the first conveyor 15 to the handing-over station 17, the first transport mechanism 13 can comprise moving devices such as, but not limited to, pushers and/or grippers capable of pushing and gripping, respectively, the vessel holders 26. Analogously, in order to transport vessel holders 26 from the handing-over station 17 to the second conveyor 16 and from the second conveyor 16 to the second storage section 8 at the handing-out level 30, the second transport mechanism 14 can comprise moving devices such as, but not limited to, pushers and/or grippers capable of pushing and gripping, respectively, the vessel holders 26.

Accordingly, the storing/retrieving device 2 can be used for storing vessel holders 26 containing to-be-processed samples in various levels in the first storage compartment 5 and for transporting vessel holders 26 to the handing-over station 17 for handing over to the analyzer 4 for analyzing samples contained in the sample vessels 3. Specifically, due to the vertical arrangement of the first storage sections 7 on various levels, a comparably large number of samples can be stored in the first storage compartment 5. Samples which have already been processed by the analyzer 4 can be handed over to the handing-over station 17 so as to be transported to and stored in various levels in the second storage compartment 6 to be unloaded upon demand. Due to the vertical arrangement of the second storage sections 8 on various levels, a comparably large number of processed samples can be stored in the second storage compartment 6. Samples which have by-passed the analyzer 4 can also be loaded into the second storage compartment 6.

For storing samples in the first and second storage compartments 5, 6, respectively, in one embodiment, the storage compartments 5, 6 can be operatively coupled to at least one cooling device 23, such as, but not limited to, a fluidic cooling device comprising a cooled fluid and one or more Peltier devices for actively cooling samples contained therein. As is known in the art, Peltier devices can function as heat pumps to absorb or generate heat according to the direction of current applied. Accordingly, samples can be stored in the storage compartments 5, 6 for a longer period without deterioration of the samples.

In one embodiment, the handing-over station 17 can comprise an in-gate for inputting vessel holders 26 from one first storage section 7 at the handing-in level 28 and an out-gate for outputting vessels holders 26 to one second storage section 8 at the handing-out level 30.

In one embodiment, the handing-over station 17 can comprise a buffer and/or a bypass section for temporarily storing vessel holders 26 before handing them over to the analyzer 4 and/or for handing over vessel holders 26 to the second storage compartment 6 bypassing the analyzer 4.

In one embodiment, the system 1 can comprise one or more sensors for sensing if the first storage sections 7 and the second storage sections 8, respectively, can be in a loaded or unloaded or partially unloaded state so as to pass vessel holders 26 containing to-be-processed samples in the first storage compartment 5 over to the analyzer 4 and to store vessel holders 26, for example, containing processed samples, in the second storage compartment 6.

As illustrated, in one embodiment, the storing/retrieving device 2 can be a modular unit which can be operatively coupled to the analyzer 4 via the handing-over station 17. Accordingly, the storing/retrieving device 2 can readily be coupled to various analyzers 4 according to the specific demands of the user. Otherwise, keeping one analyzer 4, the first and second storage sections 7, 8, respectively, can be changed according to the specific demands of the user, e.g., for increasing or reducing the storage capacity.

Figure 2A:
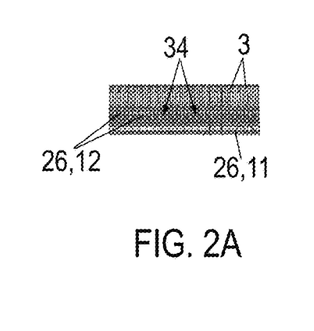
FIGS. 2A-C illustrate a longitudinal side view (FIG. 2A) and a front view (FIG. 2B) as well as a perspective view (FIG. 2C) of a tray loaded with plural racks for holding sample vessels of the system of FIGS. 1A-B according to an embodiment of the present disclosure.
Figure 2B:
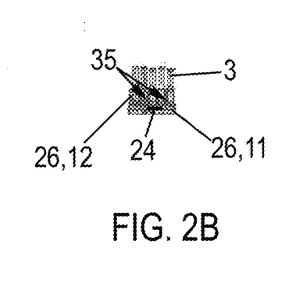
Figure 2C:
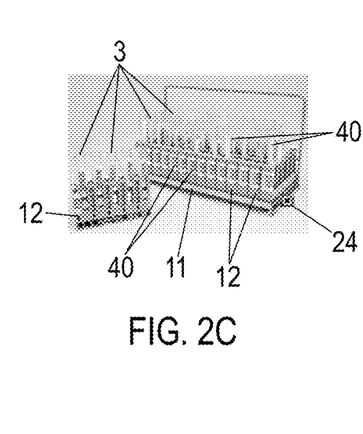

With reference to FIGS. 2A-C, in one embodiment, each vessel holder 26 can include an elongated tray 11 having a plurality of rack/holding positions 34, each of which can hold one rack 12. In one embodiment, the tray 11 can have 20 or more rack positions 34 in parallel arrangement with respect to each other. Those of skill in the art can appreciate that any other number of rack positions 34 and arrangement thereof can be envisaged according to the specific demands of the user. The racks 12 can readily be inserted into the rack positions 34 so as to be held therein and can be removed from the tray 11 by sliding them out of the rack positions 34.

In one embodiment, the tray 11 can have one or more single tube holder (holding) positions, each of which can hold one single tube holder. Accordingly, single tube holders can readily be inserted into the single tube holder positions so as to be, for example, fixedly, held therein and can be removed from the tray 11 by sliding them out of the single tube holder positions.

In one embodiment, the tray 11 can have one or more rack positions 34, each of which can hold one rack 12 and one or more single tube holder positions, each of which can hold one single tube holder. As used herein, the term "rack" can also be identified as single tube holder.

As illustrated, each elongated rack 12 can have a plurality of vessel positions 35, each of which can hold one sample vessel 3. As illustrated, in one embodiment, the rack 12 can have five vessel positions 35 serially arranged with respect to each other. Those of skill in the art can appreciate that any other number of vessel positions 35 and arrangement thereof can be envisaged according to the specific demands of the user. The sample vessels 3 can be inserted into the vessel positions 35 and can be removed from the rack 12 by sliding them out of the vessel positions 35. On the tray 11, the racks 12 can be in parallel arrangement with respect to each other, with the vessel positions 35 of each rack 12 arranged along a row perpendicular to the elongation of the tray 11. Each single tube holder can have one tube position for holding one sample tube.

As further illustrated, in one embodiment, the sample vessels 3 can be top-closed tubes, each of which can have a cap pressed into the tube for fixing. The tubes can be inserted into the rack positions 34 in an upright position. The caps can be removed from the tubes by the decapping unit 21 arranged at the first conveyor 15 and can be recapped by the recapping unit 22 arranged at the second conveyor 16. Vessel holders 26 other than top-closed tubes can be used, such as, but not limited to, sample cups.

As further illustrated in FIGS. 2B-C, in the system 1, each vessel holder 26 can have a memory tag 24 for storing/retrieving machine-readable information. In one embodiment, the memory tag 24 can be an RFID-chip allowing for a contactless writing and reading of information via radio signals typically in proximity to the memory tag 24 (near-field transmission).

With continued reference to FIGS. 2B-C, in one embodiment, the tray 11 can have the memory tag 24 that, for example, can be attached to a front-side of the tray 11. Specifically, the memory tag 24 can be used to store a tray ID, rack IDs, sample vessel IDs and/or sample IDs. Specifically, the memory tag 24 can be used to retrieve position information of sample vessels 3 with respect to the vessel positions 35 of the racks 12 on the tray 11. Each sample vessel 3 can also have a memory tag 24 for storing/retrieving machine-readable information.

With continued reference to FIG. 2C, in one embodiment, each sample vessel 3 can have a read-only tag 40 for retrieving (but not writing) machine-readable information such as, but not limited to, a barcode label indicating a sample ID and sample vessel ID, respectively. With continued reference to FIG. 2C, in one embodiment, each rack 12 can have a read-only tag 40 for retrieving (but not writing) machine-readable information such as, but not limited to, a barcode label indicating a rack ID.

Figure 3B:
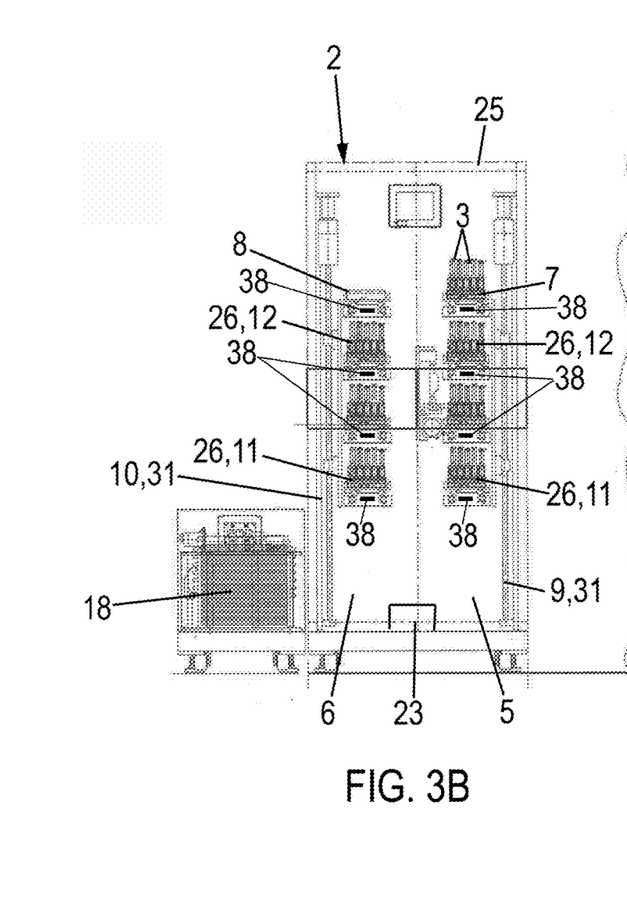
Figure 3C:
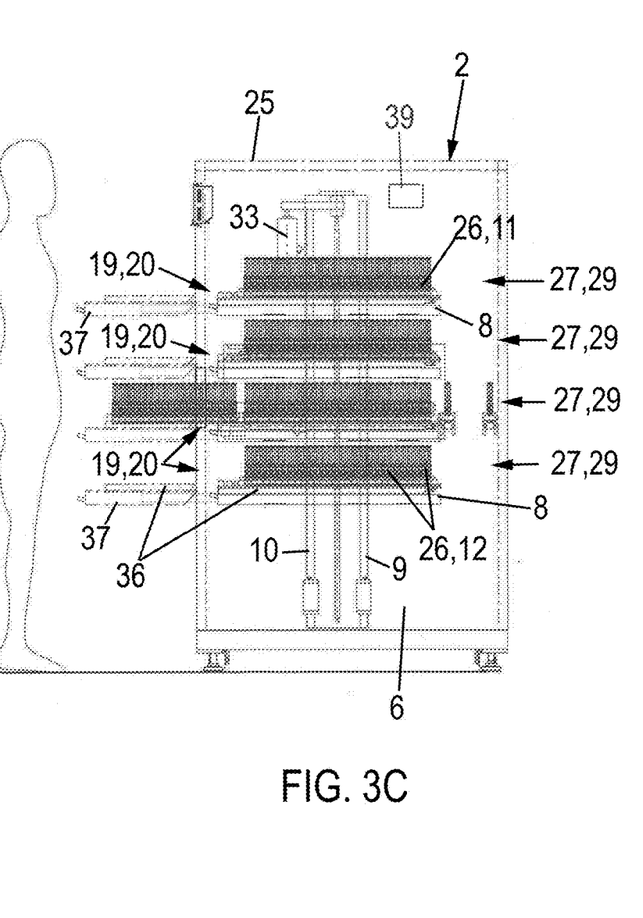

With reference to FIGS. 3A-C illustrating an exemplary system 1 for locating sample vessels using trays 11 as illustrated in FIGS. 2A-C, in one embodiment, each of the first and second storage compartments 5, 6 can comprise four first and four second storage sections 7, 8, respectively, which can be disposed in different levels vertically stacked one upon the other. Each storage section 7, 8 can be loaded with one tray 11, e.g., provided with 20 or more racks 12 for holding sample vessels 3. A lock can be used for locking/unlocking the tray 11 on the storage section 7, 8.

As indicated-above, a vertical inter-distance of the first and second storage sections 7, 8, respectively, can be changed according to the specific demands of the user, e.g., for adapting to the height of the sample vessels 3 or increasing/reducing the number of storage sections 7, 8.

As illustrated, in one embodiment, each storage section 7, 8 can comprise a pair of guiding rails 36 to slidably support one tray 11 so that the tray 11 can readily be moved along the guiding rails 36 to be inserted in or removed from the first and second storage compartments 5, 6, respectively.

With reference to FIG. 3C, in one embodiment, the housing 25 can comprise four hinged doors 37 on various levels, each of which defining one loading zone 19 and one unloading zone 20 on a same level. The doors 37 can be hinged down or up to provide access to or close the corresponding loading zone 19 of the first storage compartment 5 and unloading zone 20 of the second storage compartment 6. The number of doors 37 and the corresponding number of loading/unloading zones 19, 20 can vary according to the specific demands of the user. Particularly, only one door 37 on one level can be envisaged for loading/unloading of racks 12 and/or trays 11. The vertical distance of the doors 37 can be adapted to the vertical distance of the first and second storage sections 7, 8, respectively, so that when moving one first storage section 7 on one loading level 27 each of the remaining first storage sections 7 can simultaneously be moved on one loading level 27. Analogously, when moving one second storage section 8 on one unloading level 29, each of the remaining second storage sections 8 can simultaneously be moved on one unloading level 29.

As further illustrated, the inner side of each door 37 can also have guiding rails 36 so that a tray 11 can be put on the hinged-down door 37 to be slidably moved into the storage section 7, 8 or pulled out from the storage section 7, 8. Accordingly, the trays 11 can readily be inserted in and removed from the first and second storage compartments 5, 6, respectively, through the loading zones 19 and/or unloading zones 20. In one embodiment, the first and/or second storage sections 7, 8 respectively can be insertable in and removable from the first and second storage compartments 5, 6, respectively, through the loading zones 19 and/or unloading zones 20.

In the storing/retrieving device 2, the first storage sections 7 can be lifted up or down so as to position the first storage sections 7 on the loading levels 27 for loading with racks 12 (in the case of empty or partially loaded trays 11 already present on the first storage sections) or trays 11. Each tray 11 can be vertically translated to the handing-in level 28 for sequentially handing in racks 12 to the handing-over station 17 for handing over racks 12 holding sample vessels 3 containing to-be-processed samples to the analyzer 4. For example, by use of grippers/pushers, the racks 12 (and/or single tube holders) can sequentially be transported on the first conveyor 15 to be transported from the first storage section 7 to the handing-over station 17.

Furthermore, the second storage sections 8 can be lifted up or down so as to position one tray 11 that is empty or partially filled with racks 12 at a time on the handing-out level 30 for handing out racks 12 from the handing-over station 17 to the tray 11. For example, by use of grippers/pushers, the racks 12 (and/or single tube holders) can sequentially be brought on/removed from the second conveyor 15 to be transported in-line from the handing-over station 17 to the tray 11. Each rack-loaded tray 11 can then be lifted up or down so as to position it on one unloading level 29 for removing racks 12 and/or trays 11 from the second storage compartment 6.

In order to control the various workflows, the storing/retrieving device 2 can further include a controller 18 to operate the first translating mechanism 7 to translate a first storage section 7 one at a time to one loading level 27 for loading of racks 12 or rack-loaded trays 11 into the first storage compartment 5 and for translating rack-loaded trays 11 one at a time to the handing-in level 27, the first transport mechanism 13 for transporting racks 12 from the tray 11 on the handing-in level 27 to the handing-over station 17, the second translating mechanism 10 for translating empty or partially loaded trays 11 in the second storage compartment 6 one at a time to the handing-out level 30, the second transport mechanism 14 for transporting racks 12 from the handing-over station 17 to the tray 11 on the handing-out level 30, and the second translating mechanism 10 for translating rack-loaded trays 11 one at a time to one unloading level 29 for unloading of racks 12 or rack-loaded trays 11 from the second storage compartment 6.

The controller 18 can include a database for reading/writing (storing) inventory information, for example, with respect to individual sample vessels 3, that is to say, position information of sample vessels 3 on a vessel holder 26 with respect to the vessel positions of the vessel holder 26 as given by the racks 12 and/or single tube holders on a tray 11. The data base can also contain inventory information of racks 12 and trays 11, for example, with respect to the first and second storage sections 7, 8.

In one embodiment, the controller 18 can control a loading mode, for example, initiated by user interaction in which the first transport mechanism 13 can be operated to pause transporting of racks 12 from the first storage sections 7 to the handing-over station 17 and the first translating mechanism 9 can be operated to translate the first storage sections 7 to the loading levels 27 for loading with racks 12 or rack-loaded trays 11. The loading mode can, for example, be performed in parallel to vertically translating the second storage sections 8 one at a time to the handing-out level 30, transporting racks 12 from the handing-over station 17 to the second storage section 8 at the handing-out level 30 and vertically translating the second storage sections 8 to the unloading levels 29 for unloading of racks 12 or rack-loaded trays 11.

In one embodiment, the controller 18 can control a unloading mode, for example, initiated by user interaction in which the second transport mechanism 14 can be operated to pause transporting of racks 12 from the handing-over station 17 to the second storage sections 8 and the second translating mechanism 10 can be operated to translate the second storage sections 8 to the unloading levels 29 for unloading of racks or rack-loaded trays 11 from the second storage compartment 6. The unloading mode can, for example, be performed in parallel to vertically translating the first storage sections 7 to the loading levels 27 for loading of racks 12 or rack-loaded trays 11, vertically translating the rack-loaded trays 11 one at a time to the handing-in level 28 and transporting racks 12 to the handing-over station 17.

With reference to FIG. 3C, the storing/retrieving device 2 can have a panel 39 with an input for inputting information such as a sample ID (ID=identification) and with an output for outputting information, for example, regarding a specific status of the storing/retrieving device 2 and/or inventory information with respect to individual sample vessels 3 and samples, respectively, contained in the data base.

With continued reference to FIG. 3A, the storing/retrieving device 2 can further include a reader/writer 38 arranged on the second conveyor 16 close to the second storage compartment 6. The reader/writer 38 can read machine-readable information provided by memory tags 24 and read-only tags 40 respectively attached to the sample vessels 3 and racks 12, such as, but not limited to, barcode labels indicating sample IDs and sample vessel IDs, respectively, and rack IDs. Accordingly, an identity of each sample and/or sample vessel 3 and/or rack 12 passing the reader/writer 38 can be determined.

The reader/writer 38 can further assign the information read from the sample vessels 3 of one rack 12 concerning the sample IDs to the vessel positions 35 of the rack 12. Accordingly, samples and sample vessels 3, respectively, held by one rack 12 passing the reader/writer 38 can be mapped with respect to the vessel positions 35 of the rack 12. Hence, individual samples and sample vessels 3, respectively, can be allocated to the vessel positions 35 of the rack 12 so as to provide inventory information. Furthermore, for example, based on inventory information, the controller 18 can determine the position of the racks 12 loaded on the tray 11 at the handing-out level 30 so that the sample vessels 3 loaded on the tray 11 can be mapped with respect to the array of vessel positions 35 as given by the racks 12 on the tray 11.

Furthermore, the controller 18 can operate the reader/writer 38 to write the complete position information of samples and sample vessels 3, respectively, into the memory tag 24 of the tray 11. Accordingly, the memory tag 24 can contain position information of each sample vessel 3 on the tray 11 with respect to the array of vessel positions 35 provided by the racks 12 on the tray 11. The position information of an individual sample vessel 3 can, for example, be indicated by the rack position 34 carrying the rack 12 of the sample vessel 3 and the vessel position 35 of the rack 12 holding the sample vessel 3.

In the system 1, in one embodiment, there may not be pre-defined (predetermined) sequential arrangement of sample vessels 3 related to the vessel positions 35 of individual racks 12. Similarly, in one embodiment, there can neither be a pre-defined order of racks 12 related to the rack positions 34 of individual trays 11 nor any assignment of racks 12 to individual trays 11. Since the sample vessels 3 carry labels for identifying individual sample vessels 3 and samples contained therein, respectively, the samples can readily be assigned to test results of the analyzer 4.

Typically, each tray 11 in the second storage compartment 6 usually can carry racks 12 that have not been on one tray 11 in the first storage compartment 5. In other words, racks 12 on one tray 11 in the first storage compartment 5 usually can be distributed over plural trays 11 in the second storage compartment 6. This can, for example, be a consequence of the fact that racks 12 may contain samples supposed to be processed in a different manner so that racks 12 from one tray 11 of the first storage compartment 5 can leave the analyzer 4 in an outgoing sequential arrangement that can be different from an ingoing sequential arrangement for supplying the analyzer 4 with these racks 12.

Furthermore, the system 1 can have a sorting device for sorting sample vessels 3 with respect to vessels positions 35 of one or more racks 12. As a consequence, the sequential arrangement of sample vessels 3 relative to the vessels positions 35 of one or more racks 12 can be changed.

With reference to FIG. 3B, in one embodiment, one reader/writer 38 can be positioned in each unloading zone 20 of the second storage compartment 6 for reading information from memory tags 24 and/or read-only tags and writing information into the memory tags 24.

Specifically, the controller 18 can operate the reader/writer 38 to read information from read-only tags attached to sample vessels 3 on one tray 11 so as to identify samples and/or sample vessels 3 and to write position information (inventory information) with respect to the vessel positions 35 as given by the racks 12 into the memory tag 24 of the tray 11. Accordingly, inventory information can be stored (changed) before removing the tray 11, individual sample racks 12 and/or sample vessels 3 from the second storage compartment 6. The controller 18 can also be used to write inventory information into the controller data base.

With continued reference to FIGS. 3B-C, in one embodiment, one reader/writer 38 can be positioned in each loading zone 19 of the first storage compartment 5 for reading information from memory tags 24 and/or read-only tags and writing information into the memory tags 24. Specifically, the controller 18 can operate the reader/writer 38 to read information from read-only tags attached to sample vessels 3 on one tray 11 so as to identify samples and/or sample vessels 3 and to write position information (inventory information) with respect to the vessel positions 35 as given by the racks 12 into the memory tag 24 of the tray 11. Specifically, identification information can be read from the labels of the sample vessels 3 so as to assign the identification information to the vessel positions 35 of individual racks 12 on a tray 11. The controller 18 can also be used to write the inventory information into the controller data base.

In one embodiment, related to the case of providing a sorting device for sorting sample vessels 3 with respect to vessels positions 35 of one rack 12, the sorting device can be coupled to a reader/writer so as to read machine-readable information provided by the labels of the sample vessels 3, assign the identification information read from the sample vessels 3 to the vessel positions 35 of the rack 12 and write this information on the tray 11 supporting the rack 12.

In the following, exemplary use cases of the system 1 are described. In a first exemplary use case ("loading samples"), the user can load samples into the first storage compartment 5 while the analyzer 4 may be in operation. Specifically, the user can push a load button of the panel 39 resulting in that the storing/retrieving device 2 can pause handing-in of racks 12 to the handing-over station 17. Furthermore, the storing/retrieving device 2 can automatically detect the next loadable (empty or partly filled) tray 11 and can move this to one loading level 27. The user can then open the door 37 so as to have access to the loading zone 19. In case the user wants to select a different tray 11, this can, for example, be done by manually inputting "up" or "down" information on the panel 39 until the desired tray 11 has reached the loading zone 19. The user can then open the lock of the tray 11 in the loading zone 19, and as a result, for example, an LED can change the color, for example, to green indicating that the tray 11 in the loading zone 19 can be accessible. The user can then slide the respective tray 11 out of the loading zone 19, fill it with racks 12 and slide the rack-filled tray 11 in.

The racks 12 can also be loaded on the tray 11 in the loading zone 19. The user can then close the lock of the tray 11 so that color of the LED changes, for example, to red indicating a tray 11 in operation (not accessible). The user can then close the door 37 of the loading zone 19 and the system 1 can start its operation mode for testing the samples loaded into the first storage compartment 5. In parallel, handing-out of racks 12 from the handing-over station 17 to the second storage section 8 at the handing-out level 30 and/or unloading of sample vessels 3 from the second storage sections 8 can remain in operation. Likewise, any system alarm and error surveillance (for example, temperature control) can remain in operation. Furthermore, an inventory management including registration of rack IDs and/or sample IDs along the second conveyor 16 can remain in operation. In the first storage compartment 5, sample IDs and/or vessel IDs can be read from read-only tags on sample vessels 3, followed by writing inventory information into the memory tag 24 of the tray 11 and/or into the data base of the controller 18.

In a second exemplary use case ("unloading samples"), the user can unload trays 11 from the second storage compartment 6 while the analyzer 4 can be in operation. Specifically, the user can push an unload button of the panel 39 resulting in that the storing/retrieving device 2 can pause handing-out of racks 12 from the handing-over station 17 to the second storage section 8 at the handing-out level 30. Furthermore, the storing/retrieving device 2 can automatically detect the next fully or partially loaded tray 11 and can move this to one unloading level 29. The user can then open the door 37 to have access to the corresponding unloading zone 20. In case the user wants to select a different tray 11, this can, for example, be done by manually inputting "up" or "down" information on the panel 39 until the desired tray 11 has reached the unloading level 29. The user can then open a lock of the tray 11 in the unloading zone 20. The system can then write/read (for confirmation) logistic information (tray ID, sample ID, position) into/from the memory tag of the tray 11 in the unloading zone. After confirmation of the tray logistic information, an LED can change color to, for example, green indicating the accessible tray 11. The user can then slide the respective tray 11 out to unload with the racks 12. The tray 11 can then be slide in again. The user can then close the lock of the tray 11 resulting in changing the color of the LED, for example, to red indicating the tray 11 in operation (not accessible). The user can then input "up" or "down" information to select another tray 11 to be vertically translated to the unloading zone 20 to be unloaded. Then, the user can close the door 37 of the unloading zone 20 and the system 1 can start its operation mode for transporting sample racks 12 into the second storage compartment 6. In parallel, handing-in of racks 12 to the handing-over station 17 and/or loading of racks 12 and/or trays 11 into first storage compartment 5 can remain in operation. Likewise, any system alarm and error surveillance (for example, temperature control) can remain in operation. In the second storage compartment 5, sample IDs and/or vessel IDs can be read from read-only tags on sample vessels 3, followed by writing inventory information into the memory tag 24 of the tray 11 and/or controller data base before unloading.

A third exemplary use case ("routine operation") includes various procedures. In a first procedure ("continuous operation"), the systems 1 can detect rack-loaded trays 11 in the first storage compartment 5, transport one or more rack-loaded trays 11 sequentially to the handing-in level 28, transport racks 12 from the first storage section 7 at the handing-in level 28 to the first conveyor 15 and transport racks 12 from the first conveyor 15 to the handing-over station 17. Furthermore, the system 1 can detect empty or partially loaded trays 11 in the second storage compartment 6, transport one or more empty or partly rack-loaded trays 11 sequentially to the handing-out level 30, transport racks 12 from the handing-over station 17 to the second conveyor 16 and transport racks 12 from the second conveyor 16 to the second storage section 8 at the handing-out level 30. Furthermore, the system 1 can detect empty or partially rack-loaded trays 11 in the first storage compartment 5 and move it to one loading zone 19, and, can detect full or partially rack-loaded tray 11 in the second storage compartment 6 and move it to one unloading zone 20. For unloading trays 11, the system 1 can write/read logistic information (tray ID, sample ID, position) into the memory tag 24 of the tray 11.

In a second procedure ("loading operation"), subsequent racks 12 on one tray 11 can be transported on the first conveyor 15 so as to move the racks 12 to an in-gate of the handing-over station 17. Optionally the rack-ID and sample IDs on the rack 12 can be recognized and/or confirmed to allow inventory management of stored samples before feeding into the analyzer. The system can acknowledge and accept transfer into the in-gate of the handing-over station 17.

In a third procedure ("unloading operation"), subsequent racks 12 can be transported into an out-gate of the handing-over station 17 and then can be pushed on the second conveyor 16 to move the racks 12 to the second storage section 8 at the handing-out level 30. Optionally the rack ID and sample IDs can be recognized. Optionally the rack-ID and sample IDs can be recognized and/or confirmed to allow inventory management of stored samples before feeding into the analyzer. Subsequent racks 12 can be pushed from the second conveyor 16 to the tray 11 in the handing-out level 30. Before unloading, the tray inventory information from the controller system data base (storage for inventory information) can optionally be written before handing-out can be allowed. In a fourth procedure ("temperature control"), the temperature of the system 1 can be controlled, and, if the temperature is outside pre-determinable specifications, an error/alarm can be initiated. In a fifth procedure ("status control"), the system status can be checked and displayed on the panel 39, for example, by an icon, color code, or flashing rotating light. The number of full trays 11 (to be unloaded) or empty trays 11 (to be loaded) can be displayed. In case the system status is outside of pre-determined specifications, an error/alarm can be initiated.

In a fourth exemplary use case ("search sample ID"), the user can input a rack and/or sample ID on the panel 39. The controller 18 can then search if the input ID is in the inventory, and, if in inventory, the controller 18 can acknowledge this to the user on the panel 39, including location and interactive user workflow to ask for access to the sample. If the user selects retrieval, the system can detect a tray 11 and move this tray 11 to one unloading level 29. The user can then open the door 37 of the corresponding unloading zone 20 and can open the lock of the tray 11. The storing/retrieving device 2 can write/read logistic information (tray ID, sample ID, position) into/from the memory tag 24 of the tray 11 or from the controller database inventory. After confirmation of the logistic information, the system can switch the LED to green to indicate that the tray 11 can be accessible. The user can then slide the tray 11 out to remove the desired rack 12 and/or sample. The user can then acknowledge retrieval. The user can then slide the tray 11 back and can close the lock of the tray resulting in switching the LED to red (tray 11 in operation, not accessible). The user can then close the door 37 of the unloading zone 20 and the system can start the operation mode. In parallel, the loading/unloading process can remain in operation. Likewise, any system alarm and error surveillance (e.g. temperature control) can remain in operation.

Accordingly, when unloading a tray 11 from the second storage compartment 6, inventory information with respect to sample vessels 3 on the tray 11 can be written on the memory tag 26 of the tray 11. Furthermore, sample-IDs, rack-IDs and information concerning the time of removing the tray 11 from the second storage compartment 6 can be written on the memory tag 24. Accordingly, samples can be manually or automatically disposed after elapse of a predetermined period of time.

Furthermore, in case a sample vessel 3 is to be located within the first and second storage compartments 5, 6, respectively, and/or within the analyzer 4, the sample-ID and/or sample vessel-ID can be input by the panel 39 wherein the controller can output the position of sample vessel 3 on the panel 39 based on inventory information, for example, contained in the controller 18 data base. Accordingly, the user can get information about the location of the sample vessel 3, for example, by using a menu displayed by the panel 39.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A system, the system comprises:
   at least one analyzer for analyzing samples;
   a handing-over station coupled to the analyzer, the handing-over station comprising a stationary handing-in level for handing in vessel holders to the analyzer and a stationary handing-out level for handing over the vessel holders; and
   an automated device for storing and retrieving of the vessel holders for holding sample vessels for containing samples comprising, a first storage compartment comprising a plurality of first storage sections disposed on different levels for storing of the vessel holders;
   a first translating mechanism comprising a first vertical rod, wherein a first carrier is fixed to the first vertical rod by threaded engagement with the first vertical rod so that when the first vertical rod rotates along its longitudinal axis, the first carrier moves vertically, wherein the first storages sections are mounted to the first carrier and are vertically translated by the first carrier so as to translate one storage section at a time to a loading level of a loading zone for loading the vessel holders into the first storage compartment and to translate one storage section at a time to the stationary handing-in level of the handing-over station for handing in the vessel holders to the at least one analyzer;
   a second storage compartment comprising a plurality of second storage sections disposed on different levels for storing of the vessel holders;
   a second translating mechanism comprising a second vertical rod, wherein a second carrier is fixed to the second vertical rod by threaded engagement with the second vertical rod so that when the second vertical rod rotates along its longitudinal axis, the second carrier moves vertically, wherein the second storages sections are mounted to the second carrier and are vertically translated by the second carrier so as to translate one storage section at a time to the stationary handing-out level of the handing over station and to translate one storage section at a time to an unloading level of an unloading zone for unloading the vessel holders from the second storage compartment;
   a first transport mechanism comprising a first unidirectional conveyor for transporting the vessel holders from one of the plurality of first storage sections at the stationary handing-in level to the handing-over station;
   a second transport mechanism comprising a second unidirectional conveyor for transporting the vessel holders from the handing-over station to one of the plurality of second storage sections at the stationary handing-out level, wherein the second unidirectional conveyor is parallel to the first unidirectional conveyor; and
   a controller to operate the mechanisms.

2. The system according to claim 1, wherein the controller operates the first translating mechanism, the first transport mechanism, the second translating mechanism and the second transport mechanism in such a manner that the vessel holder is handed in from a first storage section to the handing-over station only when there is at least one empty position available in a second storage section for receiving the vessel holder from the handing-over station.

3. The system according to claim 1, wherein one of the plurality of first storage sections is insertable into and removable from the first storage compartment through the loading zone and/or from the second storage compartment through the unloading zone and/or wherein each of the plurality of first storage sections comprise a tray for holding one more racks, wherein each of the trays are insertable into and removable from the first storage compartment through the loading zone and/or from the second storage compartment through the unloading zone.

4. The system according to claim 1, wherein one of the plurality of second storage sections is insertable into and removable from the first storage compartment through the loading zone and/or from the second storage compartment through the unloading zone and/or wherein each of the plurality of second storage sections comprise a tray for holding one more racks, wherein each of the trays are insertable into and removable from the first storage compartment through the loading zone and/or from the second storage compartment through the unloading zone.

5. The system according to claim 1, wherein each of the first storage sections and each of the second storage sections are positionable in various levels so that an inter-distance between two adjacent storage sections can be changed.

6. The system according to claim 1, wherein the first conveyor has a decapping unit for decapping the sample vessels.

7. The system according to claim 1, wherein the second conveyor has a recapping unit for recapping the sample vessels.

8. The system according to claim 1, further comprising, one or more readers/writers for reading and/or writing machine-readable information from/into memory tags and/or reading machine-readable information from read-only tags attached to the vessel holders and/or the sample vessels.

9. The system according to claim 8, wherein the controller operates the one or more readers/writers for reading information from the tags so as to identify the vessel holders and/or the sample vessels for locating and/or tracing individual vessel holders and/or individual sample vessels in the first and second storage compartments; and/or the one or more readers/writers for writing information into the memory tags for making an inventory and tracing the sample vessels and/or the vessel holders; and/or the one or more readers/writers for reading information from the tags so as to identify the vessel holders and/or the sample vessels and writing information into a controller database for making an inventory and tracing the sample vessels and/or the vessel holders.

10. The system according to claim 1, further comprising, one or more sensors for sensing if the storage sections are in a loaded or in a partially unloaded state.

11. The system according to claim 1, wherein the controller controls a loading mode initiated by user interaction in which the first transport mechanism is paused and the first translating mechanism is operated for translating one or more of the plurality of first storage sections one at a time to the loading level for loading the first storage compartment with the vessel holders.

12. The system according to claim 1, wherein the controller controls an unloading mode initiated by user interaction in which the second transport mechanism is paused and the second translating mechanism is operated for translating one or more of the plurality of holder-loaded second storage sections one at a time to the unloading level for unloading of the vessel holders from the second storage compartment.

13. The system according to claim 1, wherein the automated system for storing and retrieving of the vessel holders for holding the sample vessels for containing samples is a modular device.

14. The system according to claim 1, wherein the handing-over station comprises a buffer and/or a bypass section for temporarily storing the vessel holders before handing them over to the analyzer and/or for handing over the vessel holders to the second storage compartment bypassing the analyzer.

* * * * *